(12) United States Patent
Cho et al.

(10) Patent No.: US 9,874,524 B2
(45) Date of Patent: Jan. 23, 2018

(54) IN-SITU SPATIALLY RESOLVED PLASMA MONITORING BY USING OPTICAL EMISSION SPECTROSCOPY

(71) Applicant: Applied Materials, Inc., Santa Clara, CA (US)

(72) Inventors: Tae Seung Cho, San Jose, CA (US); Junghoon Kim, Santa Clara, CA (US); Soonwook Jung, Palo Alto, CA (US); Soonam Park, Sunnyvale, CA (US); Dmitry Lubomirsky, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/061,769

(22) Filed: Mar. 4, 2016

(65) Prior Publication Data

US 2017/0254755 A1    Sep. 7, 2017

(51) Int. Cl.
| | | |
|---|---|---|
| *G01J 3/44* | (2006.01) | |
| *G01N 21/68* | (2006.01) | |
| *H01J 37/10* | (2006.01) | |
| *H01J 37/32* | (2006.01) | |

(52) U.S. Cl.
CPC .............. *G01N 21/68* (2013.01); *H01J 37/10* (2013.01); *H01J 37/32458* (2013.01); *G01N 2201/068* (2013.01); *G01N 2201/0638* (2013.01); *H01J 2237/103* (2013.01); *H01J 2237/3341* (2013.01)

(58) Field of Classification Search
CPC ........... G01N 21/68; G01N 2201/0638; G01N 2201/068; H01J 37/10; H01J 37/32458; H01J 2237/103; H01J 2237/3341; G01J 3/02; G02B 7/282
See application file for complete search history.

(56) References Cited

U.S. PATENT DOCUMENTS

| | | |
|---|---|---|
| 6,627,463 B1 | 9/2003 | Sarfaty |
| 7,169,625 B2 | 1/2007 | Davis et al. |
| 7,599,048 B2 | 10/2009 | Yoo et al. |
| 8,610,902 B2 | 12/2013 | Leung et al. |
| 2007/0229979 A1* | 10/2007 | Nurishi .................. G02B 7/282 359/697 |
| 2010/0200767 A1* | 8/2010 | Yi ............................ G01J 3/02 250/423 R |

* cited by examiner

*Primary Examiner* — Jamil Ahmed
(74) *Attorney, Agent, or Firm* — Patterson + Sheridan, LLP (57) ABSTRACT

Implementations of the present disclosure relate to a plasma chamber having an optical device for measuring emission intensity of plasma species. In one implementation, the plasma chamber includes a chamber body defining a substrate processing region therein, the chamber body having a sidewall, a viewing window disposed in the sidewall, and a plasma monitoring device coupled to the viewing window. The plasma monitoring device includes an objective lens and an aperture member having a pinhole, wherein the aperture member is movable relative to the objective lens by an actuator to adjust the focal point in the plasma using principles of optics, allowing only the light rays from the focal point in the plasma to reach the pinhole. The plasma monitoring device therefore enables an existing OES (coupled to the plasma monitoring device through an optical fiber) to monitor emission intensity of the species at any specific locations of the plasma.

19 Claims, 5 Drawing Sheets

IN-SITU SPATIALLY RESOLVED PLASMA MONITORING BY USING OPTICAL EMISSION SPECTROSCOPY

FIELD

Implementations of the present disclosure generally relate to an optical device for measuring emission intensity of plasma species in a process chamber.

BACKGROUND

Deposition and etching in a plasma environment are two of the most common steps used to form patterned layers in integrated circuit manufacturing. Controls on chemical composition and impurity levels within the process chamber are crucial to the success of these steps. To ensure that a correct quantity of film is deposited or etched, the plasma state in the process chamber needs to be monitored during a plasma process. Optical emission spectrometer (OES) is a commercially available device which is used to detect the presence and relative concentrations of various gas species in a process chamber. The optical emission spectrometer works by measuring emission intensity of the species in the plasma as a function of wavelength. The OES readings are statistically analyzed to identify gaseous species and relative concentration levels of identified gases within the process chamber. The OES readings may be used to determine a processing end-point.

However, the existing OES only provides intensity measurement of the species throughout the radial distance of the plasma. The existing OES is unable to monitor emission intensity of the species at specific locations of the plasma. Therefore, there is a need in the art to provide an improved plasma monitoring device that can provide emission intensity of the species at specific locations of the plasma.

SUMMARY

A plasma chamber having an optical device for measuring emission intensity of plasma species is described herein. In one implementation, the plasma chamber includes a chamber body defining a substrate processing region therein, the chamber body having a sidewall, a viewing window disposed in the sidewall, and a plasma monitoring device coupled to the viewing window. The plasma monitoring device includes an objective lens, and an aperture member having a pinhole, wherein the aperture member is movable relative to the objective lens by a first actuator.

In another implementation, the plasma chamber includes a chamber body defining a substrate processing region therein, the chamber body having a sidewall, a viewing window disposed in the sidewall, and a plasma monitoring device coupled to the viewing window. The plasma monitoring device includes an objective lens, an aperture member having a pinhole, wherein the aperture member is movable relative to the objective lens by a first actuator, and a first diaphragm disposed in the light path between the chamber body and the objective lens, the first diaphragm having a first adjustable aperture.

In yet another implementation, a method for monitoring a plasma in a process chamber is provided. The method includes coupling a plasma monitoring device to a viewing window disposed in a sidewall of the process chamber, wherein the plasma monitoring device includes an objective lens and a movable aperture member having a pinhole, and moving the aperture member with respect to the objective lens to change a focal point in the plasma and allow light emitted from the focal point to travel through the objective lens and impinge onto the pinhole, and analyzing characteristics of the light passing through the pinhole by an optical emission spectrometer.

BRIEF DESCRIPTION OF THE DRAWINGS

Implementations of the present disclosure, briefly summarized above and discussed in greater detail below, can be understood by reference to the illustrative implementations of the disclosure depicted in the appended drawings. It is to be noted, however, that the appended drawings illustrate only typical implementations of this disclosure and are therefore not to be considered limiting of its scope, for the disclosure may admit to other equally effective implementations.

To facilitate understanding, identical reference numerals have been used, where possible, to designate identical elements that are common to the figures. The figures are not drawn to scale and may be simplified for clarity. It is contemplated that elements and features of one implementation may be beneficially incorporated in other implementations without further recitation.

DETAILED DESCRIPTION

Figure 1:
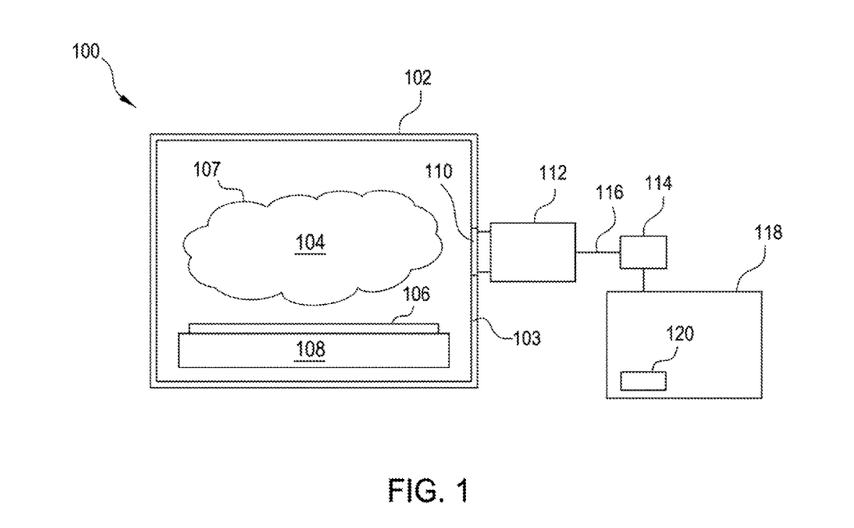
FIG. 1 illustrates a simplified cross-sectional view of an exemplary plasma chamber that may be used to practice implementations of the present disclosure.

FIG. 1 illustrates a simplified cross-sectional view of an exemplary plasma chamber 100 that may be used to practice implementations of the present disclosure. As shown in FIG. 1, the plasma chamber 100 includes a chamber body 102 defining a substrate processing region 104 therein. During a plasma process, such as a dry etch process, a substrate 106 is supported on a pedestal 108 and exposed to a plasma 107 formed in the substrate processing region 104. The plasma 107 generates electromagnetic radiation that includes emissions having wavelengths in the optical spectrum. A portion of the emissions is monitored through a viewing window 110 disposed in a sidewall 103 of the plasma chamber 100. The viewing window 110 may be comprised of glass, quartz or other suitable transparent materials through which light can be monitored. The emissions are detected by a plasma monitoring device 112 coupled to the viewing window 110. The plasma monitoring device 112 measures emission intensity of species at desired locations of the plasma. The measurement data is then transmitted to an optical emission spectrometer (OES) 114 through an optical fiber 116. The OES 114 spectrally separates incoming light rays based on measurement data and wavelength, and identifies gaseous species and relative concentration levels of identified gases within the process chamber. The OES readings from the process chamber are statistically processed in a processor 118 coupling to the OES 114 to determine a processing end-point or control of physical processing within the process chamber. The control of physical processing may be performed by executing computer instructions stored in a memory 120 resided in the processor 118.

Figure 2A:
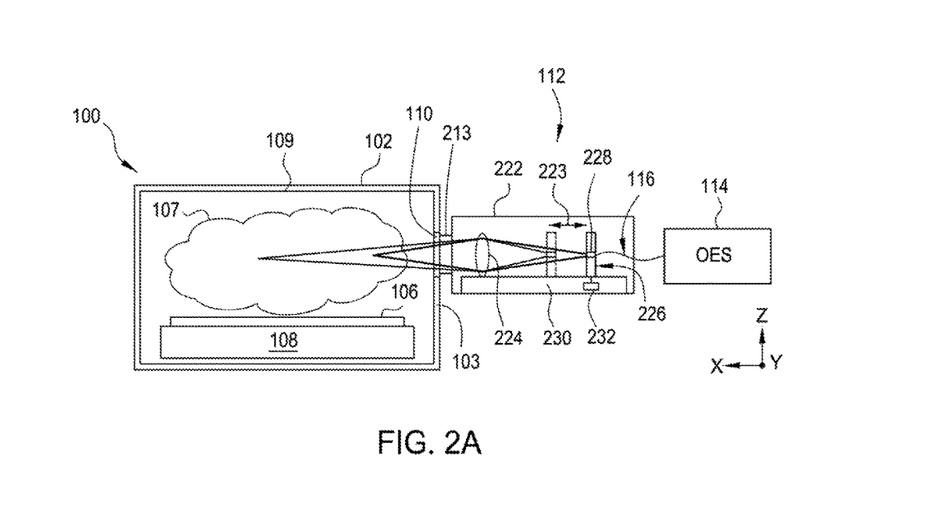
FIG. 2A illustrates a simplified cross-sectional view of a plasma monitoring device of FIG. 1 according to one implementation of the present disclosure.

FIG. 2A illustrate a simplified cross-sectional view of a plasma monitoring device 112 of FIG. 1 according to one implementation of the present disclosure. The plasma monitoring device 112 generally includes a housing 222, an objective lens 224, and an aperture member 226 having a pinhole 228. The objective lens 224 may be a converging lens, for example, a convex lens. If desired, two or more objective lens 224 (either converging lens or diverging lens) may be used in the light path to obtain desired depth of field or depth of focus. The plasma monitoring device 112 may include an inlet 213 connecting the housing 222 to the viewing window 110 disposed in the sidewall 103. The inlet 213 is sized to allow passage of the light rays from the plasma. The pinhole 228 is coupled to the optical fiber 116, which is movable together with the pinhole 228.

In some implementations, instead of separating a pinhole and an optical fiber, the aperture member 226 is coupled to an optical fiber 116 having a pinhole. Therefore, the optical fiber 116 is combined with the pinhole as an integrated unit to enhance the light intensity. In such a case, the optical fiber 116 may have a light inlet provided at one end serving as a pinhole.

The objective lens 224 and the aperture member 226 are supported by a stage 230 disposed within the housing 222. The aperture member 226 is movable relative to the objective lens 224. For example, the aperture member 226 is movable along the X-axis direction, i.e., the longitudinal direction of the housing 222, as shown by the arrow 223. In some implementations, the aperture member 226 is movable along the Y-axis direction. In some implementations, the aperture member 226 is movable along the Z-axis direction. The aperture member 226 may be movable in X-Y or X-Y-Z directions if needed.

The aperture member 226 may be driven by an actuator 232 or any other suitable mechanism directly or indirectly coupled to the housing 222. The objective lens 224 is positioned on the stage 230 in stationary manner. Alternatively, both the aperture member 226 and the objective lens are movable relative to each other along the X-axis. In such a case, the objective lens 224 may be driven by a separate actuator directly or indirectly coupled to the housing 222.

One suitable convex lens may have a wavelength range of 350 nm to 2000 nm. The convex lens may have a spherical surface power of 3π/2 (π is a desired wavelength, e.g., 633 nm) and a refractive index of 1.515 at 633 nm. The diameter of the convex lens may vary depending upon the size of the viewing window 110 of the plasma chamber 100. For example, the diameter of the convex lens may vary from 6 mm to 2 inches, which provides a focal length from 10 mm to 1 m (focal length tolerance ±1%). In one example, the convex lens is 1 inch in diameter. In another example, the convex lens is 0.5 inch in diameter. The diameter of the pinhole 228 may vary depending upon the resolution needed to obtain a desired depth of focus. For example, the diameter of the pinhole 228 may vary from 1 μm to 1 mm. In one example, the pinhole 228 is 100 μm in diameter. The pinhole 228 may be made of a stainless steel with a black oxide coating, or nickel-plated beryllium copper. The optical fiber 116 is designed to deliver light in ultraviolet or visible wavelength range (300 nm to 1100 nm) and may have a diameter of 10 μm to 600 μm, for example about 100 μm.

In operation, the plasma monitoring device 112 employs the fundamental principle of optics based on the following equation: $1/a+1/b=1/f$, where "a" is object distance, that is, the distance of a point source of light (e.g., plasma in the process chamber) from the objective lens, "b" is image distance, that is, the distance of the focus from the objective lens, and "f" is focal length, that is, the distance at which the light rays are focused when a bundle of parallel light rays enters the objective lens. As the object distance decreases (i.e., the object is moved closer to the objective lens), the image distance increases. Therefore, the object position can be changed by changing the image position.

During a plasma process, such as dry etch, light emitted from the plasma travels through the viewing window 110 and the objective lens 224. The light is then focused on the aperture member 226 by the objective lens 224. The pinhole 228 of the aperture member 226 obstructs the light that is not coming from the focal point and permits photons coming from the focal point to go through the pinhole 228 of the aperture member 226. Therefore, only the light rays from the focal point in the plasma are received and transmitted through the optical fiber 116 to the OES 114. In case where the objective lens 224 is a convex lens, since the objective lens 224 is positioned on the stage 230 in stationary manner, the focal length "f" is fixed. The location of the aperture member 226 (i.e., image distance "b") can move towards or away from the objective lens 224 to set the focal point in the plasma (i.e., object distance "a"). The optical arrangement of the plasma monitoring device 112 therefore allows for a viewer to precisely monitor and analyze the characteristics of the plasma within the plasma chamber 100 at any desired point of interest in a substantially radial direction of the plasma chamber 100.

Figure 2B:
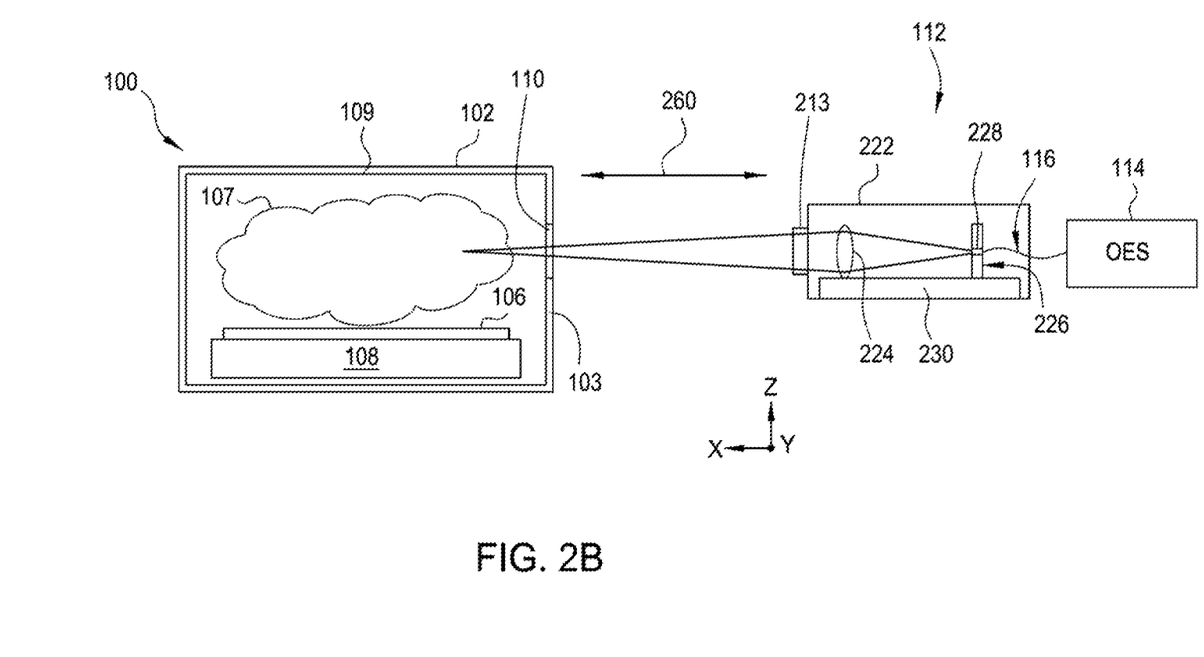
FIG. 2B illustrates a simplified cross-sectional view of an entire plasma monitoring device being movable with respect to the plasma chamber according to another implementation of the present disclosure.
Figure 4:
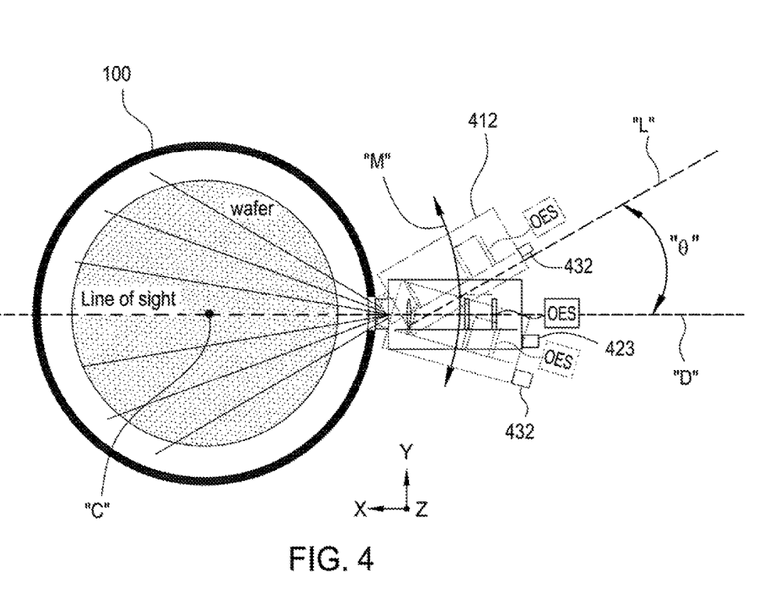
FIG. 4 illustrates a simplified top view of a plasma monitoring device according to one another implementation of the present disclosure.

In some implementations, both the objective lens 224 and the aperture member 226 may be disposed stationary within the plasma monitoring device 112. The entire plasma monitoring device 112 can be movable with respect to the plasma chamber 100 by an actuator to set a desired focal point in the plasma, as shown in FIG. 2B. In such a case, the plasma monitoring device 112 may be movable towards or away from the plasma along the X-axis direction, i.e., the longitudinal direction of the housing 222, as shown by the arrow 260. In some implementations, the plasma monitoring device 112 is movable along the Y-axis direction. In some implementations, the plasma monitoring device 112 is movable along the Z-axis direction. Alternatively, the plasma monitoring device 112 may be movable in X-Y or X-Y-Z directions. In some implementations, the plasma monitoring device 112 may be pivotally movable about a Z-axis direction of the plasma chamber 100. The Z-axis direction is parallel to a central axis "C" vertically passing through the plasma chamber 100, as shown in FIG. 4. The implementation shown in FIG. 2B can also be applied or incorporated into the plasma monitoring device 312, 412, 512 and 612.

Figure 3A:
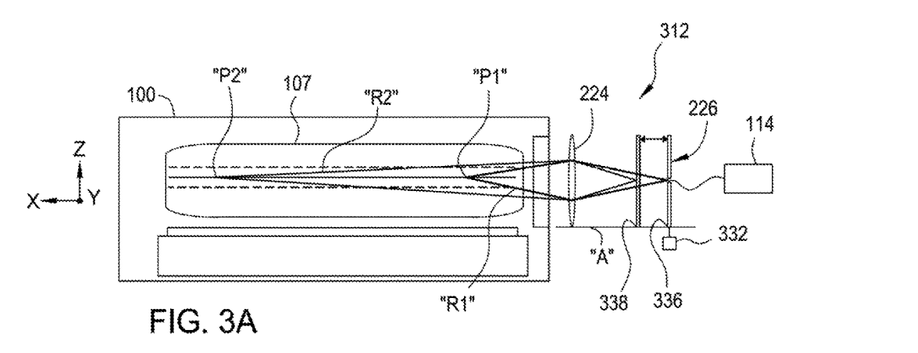
FIGS. 3A-3C illustrate possible paths of travel of the light rays when moving aperture member according to implementations of the present disclosure.
Figure 3B:
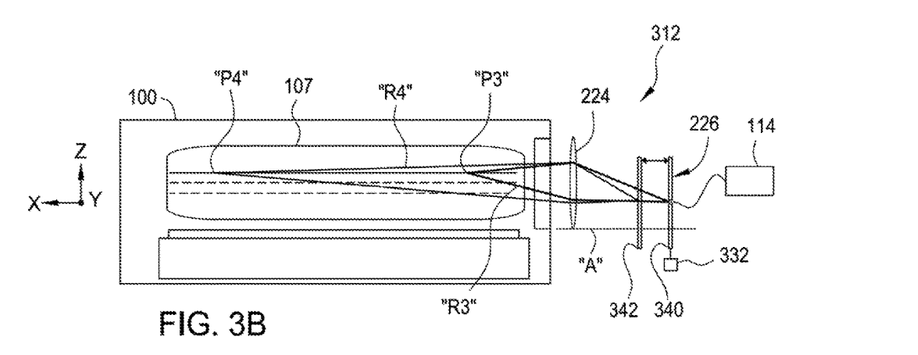
Figure 3C:
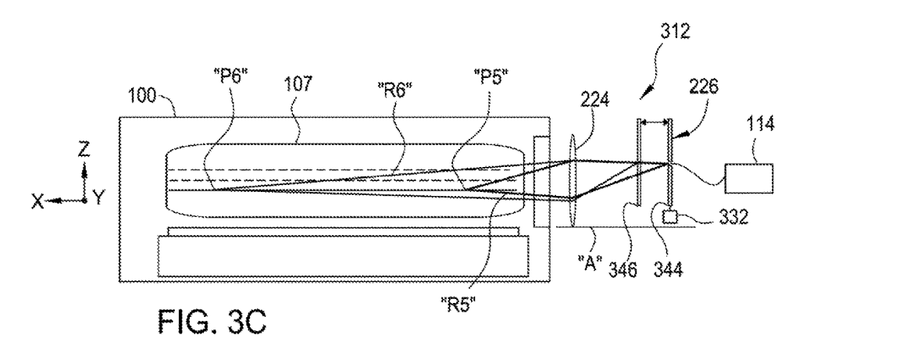

FIGS. 3A-3C illustrate an exemplary plasma monitoring device 312 according to implementations of the present disclosure. The plasma monitoring device 312 is substantially identical to the plasma monitoring device 112 except that the aperture member 326 is movable two-dimensionally, thereby enabling horizontal and vertical monitoring capability in the plasma chamber 100. For the sake of clarity, the housing and the stage as those shown in FIG. 2 have been omitted. In this implementation, the aperture member 226 is moved horizontally and vertically with respect to the objective lens 224 by, for example, a two-axis actuator 332 as shown, two separated actuators, or any other suitable mechanism, such as an X-Y stage with the capability of vertical "Z" motion. In any case, the aperture member 226 is movable towards or away from the plasma horizontally along the X-axis direction (i.e., the longitudinal direction of the housing). The aperture member 226 is also movable vertically along the Z-axis direction (i.e., the height direction of the housing). Since the objective lens 224 is fixed, moving of the aperture member 226 horizontally and/or vertically changes the corresponding focal point in the plasma according to principles of optics. The plasma monitoring device 312 therefore provides the profile of the plasma at different radial distances along the X-axis direction and the profile of the plasma at different heights along the Z-axis direction in the plasma chamber 100, as will be discussed in more detail below.

FIG. 3A depicts possible paths of travel of the light rays when moving the aperture member 226 horizontally in one implementation. When the aperture member 226 and the objective lens 224 are both supported by an actuator 332 positioned on a common surface "A" at a first position 336, the aperture member 226 can capture light rays emitting along a path of travel "R1" from a first focal point "P1" in an intermediate radial extent of the plasma 107. When the aperture member 226 moves towards the objective lens 224 to a second position 338, the aperture member 226 can capture light rays emitting along a path of travel "R2" from a second focal point "P2" in the intermediate radial extent of the plasma 107. While not shown, it is contemplated that the common surface "A" shown in FIGS. 3A-3C can be a support surface (if it is supported by an actuator or stage) or a reference surface within the plasma monitoring device 312.

FIG. 3B depicts possible paths of travel of the light rays when moving the aperture member 226 vertically and horizontally in another implementation. When the stationary objective lens 224 is supported on the common surface "A" and the aperture member 226 is supported by the actuator 332 positioned below the common surface "A" at a third position 340, the aperture member 226 can capture light rays emitting along a path of travel "R3" from a third focal point "P3" in the upper radial extent of the plasma 107. When the aperture member 226 moves towards the objective lens 224 to a fourth position 342, the aperture member 226 can capture light rays emitting along a path of travel "R4" from a fourth focal point "P4" in the upper radial extent of the plasma 107.

FIG. 3C depicts possible paths of travel of the light rays when moving the aperture member 226 vertically and horizontally in yet another implementation. When the stationary objective lens 224 is supported on the common surface "A" and the aperture member 226 is supported by the actuator 332 positioned above the common surface "A" at a fifth position 344, the aperture member 226 can capture light rays emitting along a path of travel "R5" from a fifth focal point "P5" in the bottom radial extent of the plasma 107. When the aperture member 226 moves towards the objective lens 224 to a sixth position 346, the aperture member 226 can capture light rays emitting along a path of travel "R6" from a sixth focal point "P6" in the bottom radial extent of the plasma 107.

FIG. 4 illustrates a simplified top view of a plasma monitoring device 412 according to one another implementation of the present disclosure. The plasma monitoring device 412 is substantially identical to the configuration of the plasma monitoring device 112 or 312 except that the plasma monitoring device 412 is pivotally movable about a Z-axis direction of the plasma chamber 100. The Z-axis direction is parallel to a central axis "C" vertically passing through the plasma chamber 100. In one implementation, the plasma monitoring device 412 is pivotally movable about the Z-axis direction such that a longitudinal axis "L" of the plasma monitoring device 412 or the housing 422 forms an angle "θ" in the range of about ±60 degrees with respect to an imaginary diameter line "D" of the plasma chamber 100 passing through the viewing window 110. The angle "θ" may vary so long as the plasma monitoring device 412 is positioned such that a line of slight can pass directly from any point in the plasma to the objective lens and aperture member of the plasma monitoring device 412. In various examples, the angle "θ" may be in the range of about ±50 degrees, about ±45 degrees, about ±40 degrees, about ±35 degrees or about ±30 degrees.

An actuator 432 or other suitable mechanism may be used to provide pivotal movement of the plasma monitoring device 412, as indicated by the arrow "M". In some implementations, the actuator 432 may work with a separate actuator (such as the actuator 332 as discussed above with respect to FIGS. 3A-3C) to provide the plasma monitoring device 412 with an adjustable X-Z translational motion as well as rotational motion about the Z-axis. Alternatively, the actuator 432 may be an X-Y stage with the capability of vertical and rotational motion. The plasma monitoring device 412 therefore provides lateral angular measurement of the plasma intensity within the plasma chamber 100 at any desired locations and azimuth angles.

It is contemplated that the plasma monitoring device discussed in FIGS. 2 to 4 can optionally be disposed at a location other than the sidewall of the plasma chamber. For example, the plasma monitoring device may be positioned at a ceiling of a plasma chamber, such as the ceiling 109 shown in FIG. 2. This arrangement of the plasma monitoring device enables measurement of the plasma intensity from the top of the plasma chamber.

Figure 5:
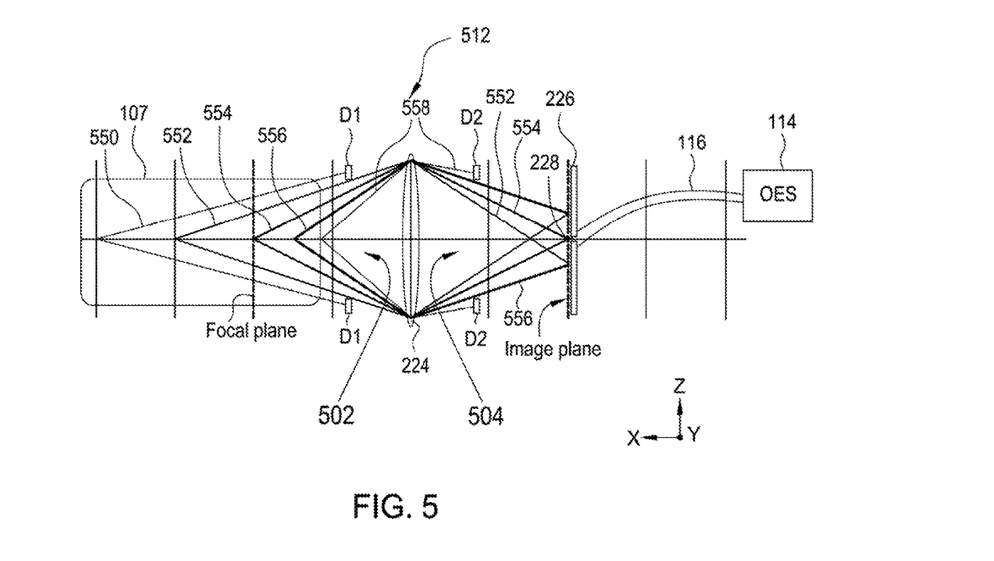
FIG. 5 illustrates a simplified cross-sectional view of a plasma monitoring device having diaphragms according to one implementation of the present disclosure.

To enhance the depth of field and depth of focus of the plasma monitoring device, one or more diaphragms may be disposed in the light path to block unwanted rays of light from reaching the image plane. The terms "depth of field" and "depth of focus" are readily understood by those skilled in the art as referring to the range of distance in front and back of the selected focusing distance throughout which a satisfactory image is obtained. FIG. 5 illustrates a simplified cross-sectional view of a plasma monitoring device 512 having diaphragms according to one implementation of the present disclosure. The plasma monitoring device 512 is substantially identical to the plasma monitoring device 112 except that diaphragms are added in the light path before and/or after the objective lens to block unwanted rays of light from reaching the image plane. The term "light path" refers to the path along with light may travel and intersect the objective lens and the aperture member. For ease of illustration, description below will be based on the plasma monitoring device 112 of FIG. 2, and only relevant components are shown and discussed. The implementation of FIG. 5 can also be applied or incorporated into the plasma monitoring device 312 and 412.

As shown in FIG. 5, a first diaphragm D1 is disposed in between the plasma 107 and the objective lens 224, and a second diaphragm D2 is disposed in between the objective lens 224 and the aperture member 226. The first diaphragm D1 has an aperture 502 sized to block a portion of the light from far outside the focal plane of the objective lens 224. Therefore, the light rays at and inside the focal plane, for example light rays 554, 556, and 558, are permitted to travel through the objective lens 224. The light ray 550 is blocked by the first diaphragm D1. Similarly, the second diaphragm D2 has an aperture 504 sized to block a portion of the light from far inside the focal plane of the objective lens 224. Therefore, the light ray 558 is blocked by the second diaphragm D2. The aperture diameter of the first diaphragm D1 and the aperture diameter of the second diaphragm D2, as well as the location of the first and second diaphragms D1 and D2 are configurable according to principles of optics so that only the light rays in the plasma at and near the focal plane, i.e., light rays 552, 554 and 556, can pass through the diaphragms and impinge on a region near the pinhole 228.

The portion of the light rays from near the focal plane can also be blocked by the pinhole 228 of the aperture member 226. In this way, only the light rays in the plasma 107 at and near the focal plane are allowed to travel to a region at and near the pinhole 228. Since only the plasma at the focal plane, i.e., light rays 554, is transmitted and monitored, the unwanted lights received at the OES 114, e.g., light rays 550, 552, 556, and 558, are avoided or greatly reduced. As a result, the measurement of the plasma intensity in the plasma chamber can be done more efficiently.

It is understood that the number of the diaphragm may vary as needed. While two diaphragms are shown, more or less diaphragm is also contemplated. In some implementations, the first diaphragm D1 or the second diaphragm D2 may be omitted. In some implementations, two or more diaphragms may be disposed in the light path before and/or after the objective lens to control rays of light from reaching the aperture member 226 using principles of optics.

Figure 6:
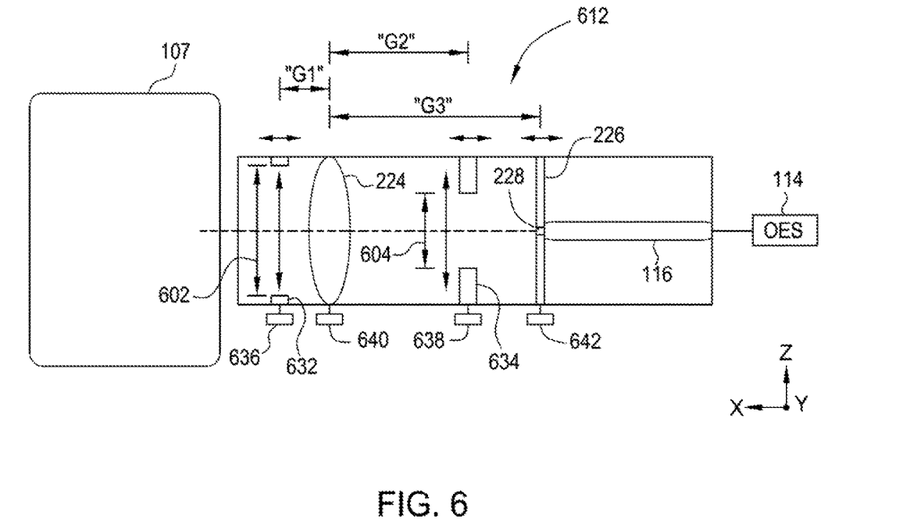
FIG. 6 illustrates a simplified cross-sectional view of a plasma monitoring device according to yet another implementation of the present disclosure.

FIG. 6 illustrates a simplified cross-sectional view of a plasma monitoring device 612 according to yet another implementation of the present disclosure. The plasma monitoring device 612 is substantially identical to the plasma monitoring device 512 except that the diaphragms are movable along the X-axis direction and the aperture diameter of each of the diaphragms is adjustable along the Z-axis direction. In one implementation, the first diaphragm 632 is disposed in between the plasma 107 and the objective lens 224, and a second diaphragm D2 is disposed in between the objective lens 224 and the aperture member 226. The first diaphragm 632 may be spaced apart from the objective lens 224 by a distance "G1". The second diaphragm 634 may be spaced apart from the objective lens 224 by a distance "G2". The aperture member 226 may be spaced apart from the objective lens 224 by a distance "G3". The distance "G1" may be equal to, smaller, or larger than the distance "G2". The distance "G3" may be equal to, smaller, or larger than the distance "G1". The distance "G3" may be equal to, smaller, or larger than the distance "G2". Distances "G1", "G2" and "G3" are configurable to obtain desired light path of travel according to principles of optics.

The first diaphragm 632 has an aperture 602 sized to block a portion of the light from outside the focal plane. The location of the first diaphragm 632 can be changed to adjust the depth of field. Since the first diaphragm 632 is positioned closer to the objective lens 224, light rays out-of-focus are blocked from reaching the aperture member 226. Likewise, the second diaphragm 634 has an aperture 604 sized to block a portion of the light from inside the focal plane. Since the second diaphragm 634 is positioned further away from the objective lens 224 than the first diaphragm 632, the light rays in-focused are blocked from reaching the aperture member 226. The diameter of the aperture 602 may be wider than the diameter of the aperture 604 as shown, or vice versa, depending upon the application.

If desired, the first diaphragm 632 and the second diaphragm 634 may be movable towards or away the plasma 107 along the X-axis direction to dynamically adjust the depth of field and/or depth of focus during process. The first diaphragm 632 may be movable relative to the second diaphragm 634 during process. Alternatively, the first and second diaphragms 632 and 634 may be movable concurrently or non-concurrently with respect to the objective lens 224 during process. The movement of the first and second diaphragms 632 and 634 can be achieved by the respective actuator 636, 638 as shown or a single actuator. The objective lens 224 may be stationary or movable relative to aperture member 226 by an actuator 640. The aperture member 226 is movable by an actuator 642. It is contemplated that any other suitable mechanism, such as an X-Y stage, can be used to provide lateral and/or vertical movement to the diaphragms, objective lens and the aperture member. The aperture diameter and the position of the diaphragms, objective lens and the aperture member are configurable in order to allow light rays of interests in the plasma to impinge on the aperture member 226 using fundamental principles of optics.

It is contemplated that the implementation of FIG. 6 can also be applied or incorporated into the plasma monitoring device 312 and 412 to provide plasma profile of different heights and/or different azimuth positions.

Benefits of the present disclosure include an efficient, precise measurement of emission intensity in a plasma chamber by using at least an objective lens and a pinhole disposed between a viewing window and an OES. The pinhole is movable towards or away from the objective lens to adjust the focal point in the plasma using fundamental principles of optics, allowing only the light rays from the focal point in the plasma to reach the pinhole. The pinhole can also move vertically and pivotally with respect to the objective lens to provide lateral measurement of the emission intensity within the plasma chamber at any desired locations and azimuth angles. One or more movable diaphragms may optionally be disposed in the light path before and/or after the objective lens to block unwanted rays of light from reaching the pinhole, resulting in efficient measurement of the emission intensity in the plasma chamber with minimum noise impact. The plasma monitoring device therefore enables an existing OES to monitor emission intensity of the species at any specific locations of the plasma.

While the foregoing is directed to implementations of the present disclosure, other and further implementations of the disclosure may be devised without departing from the basic scope thereof.

The invention claimed is:

1. A plasma chamber, comprising:
   a chamber body defining a substrate processing region therein, the chamber body having a sidewall;
   a viewing window disposed in the sidewall;
   a plasma monitoring device coupled to the viewing window, the plasma monitoring device comprising:
      an objective lens; and
      an aperture member, wherein the aperture member is movable relative to the objective lens by a first actuator; and
   a pivoting actuator for pivotally moving the plasma monitoring device about a central axis direction vertically passing through the chamber body.

2. The plasma chamber of claim 1, wherein the objective lens is a converging lens.

3. The plasma chamber of claim 1, wherein the aperture member has a pinhole, and the aperture member is coupled to an optical fiber at the pinhole.

4. The plasma chamber of claim 1, wherein the aperture member is coupled to an optical fiber, and the optical fiber has a pinhole integrated therein at one end.

5. The plasma chamber of claim 3, further comprising:
an optical emission spectrometer coupled to the plasma monitoring device through the optical fiber.

6. The plasma chamber of claim 1, wherein the objective lens is movable horizontally by a second actuator.

7. The plasma chamber of claim 1, wherein the aperture member is movable horizontally and vertically with respect to the objective lens.

8. The plasma chamber of claim 1, wherein a longitudinal axis of the plasma monitoring device forms an angle in the range of about ±60 degrees with respect to an imaginary diameter line of the chamber body passing through the viewing window.

9. A plasma chamber, comprising:
a chamber body defining a substrate processing region therein, the chamber body having a sidewall;
a viewing window disposed in the sidewall;
a plasma monitoring device coupled to the viewing window, the plasma monitoring device comprising:
an objective lens;
an aperture member having a pinhole, wherein the aperture member is movable relative to the objective lens by a first actuator; and
a first diaphragm disposed in a light path between the chamber body and the objective lens, the first diaphragm having a first adjustable aperture; and
a pivoting actuator pivotally moving the plasma monitoring device about a central axis direction vertically passing through the chamber body.

10. The plasma chamber of claim 9, wherein the first diaphragm is movable with respect to the objective lens.

11. The plasma chamber of claim 9, further comprising:
a second diaphragm disposed in the light path between the objective lens and the aperture member, wherein the second diaphragm has a second adjustable aperture.

12. The plasma chamber of claim 11, wherein the second diaphragm is movable with respect to the objective lens.

13. The plasma chamber of claim 9, wherein the objective lens is movable with respect to the aperture member by a second actuator, and the aperture member is movable horizontally and vertically with respect to the objective lens.

14. A method for monitoring a plasma in a process chamber, comprising:
coupling a plasma monitoring device to a viewing window disposed in a sidewall of the process chamber, wherein the plasma monitoring device comprising:
an objective lens; and
an aperture member having a pinhole;
moving pivotally the plasma monitoring device about a central axis direction vertically passing through the process chamber and moving the aperture member with respect to the objective lens to change a focal point in the plasma and allow light emitted from the focal point to travel through the objective lens and impinge onto the pinhole; and
analyzing characteristics of the light passing through the pinhole by an optical emission spectrometer.

15. The method of claim 14, further comprising:
moving the aperture member horizontally and vertically with respect to the objective lens to change a focal point to different heights in the plasma.

16. The method of claim 14, further comprising:
moving a first diaphragm disposed in a light path between the process chamber and the objective lens, the first diaphragm having a first aperture sized to block a portion of the light from outside a focal plane of the objective lens.

17. The method of claim 16, further comprising:
moving a second diaphragm disposed in a light path between the objective lens and the aperture member, the second diaphragm having a second aperture sized to block a portion of the light from inside the focal plane of the objective lens.

18. The method of claim 14, further comprising:
determining a processing end-point based on the analyzed characteristics of the light from the optical emission spectrometer.

19. The plasma chamber of claim 4, further comprising:
an optical emission spectrometer coupled to the plasma monitoring device through the optical fiber.

* * * * *